United States Patent [19]

Anello et al.

[11] Patent Number: 4,517,002

[45] Date of Patent: May 14, 1985

[54] PHOSPHORODIAMIDE UREASE INHIBITORS AND UREASE INHIBITED UREA BASED FERTILIZER COMPOSITIONS

[75] Inventors: Louis G. Anello, Hamburg; Michael Van Der Puy, Cheektowaga; Larry L. Hendrickson, Camillus, all of N.Y.; Milorad M. Rogic, Whippany, N.J.; Michael D. Swerdloff, Parsippany, N.J.; Jaroslav F. Kolc, Randolph Township, Morris County, N.J.

[73] Assignee: Allied Corporation, Morris Township, Morris County, N.J.

[21] Appl. No.: 475,989

[22] Filed: Mar. 16, 1983

[51] Int. Cl.³ ............................................... C05C 9/00
[52] U.S. Cl. ............................................ 71/28; 71/902
[58] Field of Search .................................. 71/11, 27–30, 71/902

[56] References Cited

U.S. PATENT DOCUMENTS 4,182,881  1/1980  Bayless et al. ................. 546/22
4,222,948  9/1980  Alaimo et al. ............. 260/397.7 R
4,225,526  9/1980  Alaimo et al. ............. 260/397.7 R
4,242,325 12/1980  Bayless et al. ................. 424/210

FOREIGN PATENT DOCUMENTS 830800  3/1960  United Kingdom .
1494774 12/1977  United Kingdom .

OTHER PUBLICATIONS

1978, CA, vol. 89, Abst. #89:89455k, Matzel et al.
1979, CA, vol. 90, Abst. #90:21340j, Oertal et al.
1979, CA, vol. 91, Abst. #91:122724p, Matzel et al.
1979 CA, vol. 91, Abst. #91:139619f, Heber et al.
1981, CA vol. 94, Abst. #94:101951g, Vlek et al.
1981, CA, vol. 94, Abst. #94:139429f, Bayless et al.

Primary Examiner—Ferris H. Lander
Attorney, Agent, or Firm—Richard C. Stewart, II

[57] ABSTRACT

Novel urease inhibiting phosphorodiamide compounds, urea based fertilizer compositions including such compounds, and methods and composition for using said compounds to inhibit the catalytic activity of urease.

48 Claims, No Drawings

PHOSPHORODIAMIDE UREASE INHIBITORS AND UREASE INHIBITED UREA BASED FERTILIZER COMPOSITIONS

BACKGROUND OF THE INVENTION

1. Field of the Invention

This invention relates to phosphorodiamide urease inhibitors and urease inhibited urea based fertilizer compositions. More particularly, this invention relates to urease inhibited urea based fertilizer compositions which contain certain phosphorodiamide compounds as the urease inhibitors, and to methods of and compositions for inhibiting the catalytic activity of urease through application of such compounds to the some plant growth media.

2. The Prior Art

It is well known in the art to use urea and urea compositions in fertilizers, for application to the soil. The effective life of such fertilizers, however, is of short duration wherever microbiological activity exists in the soil to which the fertilizer is applied. This is due to the fact that urea is hydrolyzed rapidly, and nitrogen is lost in the form of ammonias, when urea is placed under or on the surface of moist soil which contains urease. Urease, a crystallizable enzyme occurring in numerous bacteria and fungi, as for example *Micrococcus urease,* catalyzes the conversion of urea into ammonia and carbon dioxide. The reactions are as follows:

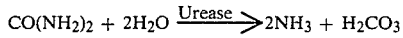

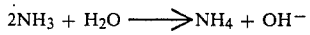

A portion of the ammonia thus formed is held by absorbing constituents of the soil and is available to plants as nutrient. However, a large amount of the ammonia may be lost to the air. A further problem resulting from the action of urease is that the accumulation of ammonium in the soil and rise in problems, including damage to germinating seedlings and young plants.

One approach to reduction of problems resulting from the activity of soil urease toward soil applied urea is to find compounds that inhibit urease activity when applied to soils in conjunction with fertilizer urea. This approach has received considerable attention, and several classes of compounds have been used as urease inhibitors.

For example some prior art describes various phosphoro compounds which are useful as urease inhibitors. Illustrative of such prior art are East German Pat. Nos. 142,714, 212,026, 122,177, 122,621 and 130,936 and Great Britain Pat. No. 1,494,774 describe various phosphorodiamidate compounds as urease inhibitors. U.S. Pat. No. 4,242,325 describes a method of controlling the enzymatic decomposition of urea to ammonia and carbonic acid due to the action of urease which comprises exposing the enzyme to certain phosphorotriamide compounds. U.S. Pat. No. 4,182,881 describes the use of certain N-[diamino-phosphinyl]arylcarboxyamide compounds as inhibitors of the enzyme urease in the urinary tract. U.S. Pat. No. 4,225,526 describes the use of 8-[(4-aminophenyl)sulfonyl]amino-2-napthalenyl phosphorodiamidate compounds as inhibitors of the enzyme urease, and U.S. Pat. No. 4,222,948 describes the use of [(4-aminophenyl)sulfonyl]amino]phenyl phosphorodimidates as inhibitors of the enzyme urease.

Still other prior art describes the use of certain phosphorotriamidate compounds for other purposes. For example, Great Britain Pat. No. 830,800 describes certain phosphorotriamidates compounds which are useful as flame proofing agents.

SUMMARY OF THE INVENTION

In accordance with the present invention, there is provided a unique fertilizer composition comprising urea or a compound which is capable of forming urea when subjected to the use conditions of the composition and a "urease inhibiting effective amount" of one or more phosphorodiamide compounds of the formula:

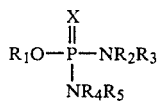

wherein
X is oxygen or sulfur;
$R_1$ is alkyl, aralkyl, cycloalkyl, heterocycle, cycloalkenyl, alkenyl or alkynyl either unsubstituted or substituted with one or more halo, hydroxy, thiocyano, heterocycle, alkylamino, dialkylamino, alkoxy, nitro, isocyano, quaternary ammonium, arylamino, alkanoyl, trihalomethyl, aryloxy, cyano, amino, isocyanato, acyloxy, $-ONO_2$, $-SO_2OH$, mercapto, arylmercapto, alkylmercapto, carboxyalkyl, $-OPO(OH)_2$, $-OB(OH)_2$ or $-OPO(OR)OH$, $-OPO(OR)_2$, $-OSO_2OR$, $-SO_2R$, and $-OSO_2R$, wherein R is aliphatic or aryl, or a combination thereof; and
$R_2$, $R_3$, $R_4$ and $R_5$ are individually hydrogen, or alkyl having from 1 to about 4 carbon atoms. In the present specification and claims, the term "phosphorodiamide compounds" is used to refer to the above referenced compounds.

Another aspect of this invention relates to a method of enhancing the yield and/or growth of plants by distributing the composition of this invention to the "plant growth media" in which the plants are being grown within reach of the root system of the plants (hereinafter referred to as "root zone"). As used herein, the term "plant growth media" refers to the various natural and artificial media which support plant growth, including but not limited to soil, potting mixtures of organic and inorganic matter, and artificial media such as polyurethane foam.

Yet another aspect of this invention relates to a method of inhibiting the ureas catalyzed hydrolysis of urea in some plant growth media which comprises distributing a "urease inhibiting effective amount" of one or more of the above-mentioned phosphorodiamide compounds in the plant growth media prior to, after or in conjunction with the application of urea to said plant growth media. Still another aspect of this invention relates to a composition comprising a "urease inhibiting effective amount" of one or more of such phosphorodiamide compounds useful for carrying out such method. As used herein, a "urease inhibiting effective amount" is an amount of such phosphorodiamide compounds which when distributed in a plant growth media is capable of inhibiting the urease catalyzed hydrolysis of urea applied to said media to any extent.

It has been discovered that by distributing a urease inhibiting effective amount of one or more of the aforementioned phosphorodiamide compounds in the said plant growth media, the urease catalyzed hydrolysis of urea to ammonia is suppressed, thereby retarding the rate at which urea is lost from the media. Furthermore, by proper distribution of the one or more phosphorodiamide compounds in the plant growth media, this action of inhibiting the hydrolysis of urea to ammonia is effective over a prolonged period of time.

DETAILED DESCRIPTION OF THE INVENTION

The application of a urease inhibiting effective amount of one or more of the above-identified phosphorodiamide compounds to a plant growth media is essential for the practice of this invention. Preferably, the amount of the one or more phosphorodiamide compound employed is sufficient to inhibit the urease catalyzed hydrolysis of all urea present in the plant growth media. Usually these goals can be achieved if the composition contains at least about 0.01 parts of said one or more phosphorodiamide compounds per million parts of said plant growth media. Hereinafter the abbreviation "p.p.m." will be used to refer to parts by weight of one or more phosphorodiamide compounds per one million parts by weight of plant growth media. In the preferred embodiments of this invention, the amount of said one or more phosphorodiamide compounds distributed in said plant growth media is from about 0.01 to about 5000 p.p.m., and in the particularly preferred embodiments is from about 2 to about 1000 p.p.m. Amongst these particularly preferred embodiments, most preferred are those embodiments in which the amount of said one or more phosphorodiamide compounds distributed in said plant growth media is from about 1 to about 500 p.p.m.

Within the above referenced limits, the particular amounts of one or more phosphorodiamide compounds used are dependent upon the particular situation. Thus, in determining the amount to be employed, consideration is made not only of the treatment need, i.e., soil pH, temperature, soil type, etc., but also of the mode of application to soil. When the one or more phosphorodiamide compounds is to be applied in a broadcast application, the amount in p.p.m. may frequently be less than in row or band applications where, for a substantial depth and width within the vicinity of application, there can be a very high concentration of the one or more phosphorodiamide compounds. When application is made near the root zone of growing plants, or when application is made immediately prior to seeding or transplanting, the amounts supplied are frequently at a lower rate than when application is made at the end of the growing season to prepare the soil for the following season. By dispersing very large dosages in growth media, a prolonged inhibition of the activity of urease can be obtained over a period of many months. The concentration of the active one or more phosphorodiamide compounds is eventually reduced to a minimum by decomposition in the soil.

In one method for carrying out the present invention, the one or more phosphorodiamide compounds are distributed throughout the growth media in a broadcast application such as by spraying, dusting, distributing in irrigation water, and the like. In such application, the one or more phosphorodiamide compounds are supplied in amounts sufficient to permeate the growing area of the plant growth medium with a urease inhibiting effective amount of such compounds. In field administration, the one or more phosphorodiamide compounds can be distributed in an soil in the amount and through such cross-section of the plant growth medium as to provide for the presence therein of a urease inhibiting effective amount of such compounds. It is usually preferred that the one or more phosphorodiamide compounds be distributed below the surface of the plant growth medium.

In another method for carrying out the present invention, the one or more phosphorodiamide compounds are administered to the plant growth medium in a band or row application. In such application, administration is made with or without carrier in amounts sufficient to supply to soil or growth medium a urease inhibiting effective amount of the one or more phosphorodiamide compounds. After administration with or without discing or dragging, subsequent irrigation or rainfall distributes the one or more phosphorodiamide compounds throughout the growth medium.

In one embodiment of the present invention, the one or more phosphorodiamide compounds is distributed throughout the plant growth media prior to seeding or transplanting the desired crop plant.

In another embodiment, the soil in the root zone of growing plants is treated with the one or more phosphorodiamide compounds in an amount effective to inhibit the activity of urease but sublethal to plant growth. By following such practice, no adverse effect is exerted by the one or more phosphorodiamide compounds upon growth of seeds or plants. Oftentimes, it is desirable to treat the soil adjacent to plants, and this procedure may be carried out conveniently in side-dressing operations.

In a further embodiment, soil can be treated with the products following harvest or after following to prevent rapid loss of urea. Such practice conserves the soil nitrogen for the following growing season. In such application, the upper limit is primarily an economic consideration.

In an additional embodiment, the soil is treated with one or more phosphorodiamide compounds in conjunction with the application of urea or a compound capable of forming urea in situ on application to the plant growth media. Urea is a well known, commercially available compound and will not be discussed herein in detail. Illustrative of compounds which are believed to form urea on addition to the soil and are water soluble and formaldehyde condensation products, as for example methylolureas, methyleneureas and mixtures thereof. These products and a method for their preparation is described in detail in U.S. Pat. No. 3,462,256. Still other useful sources of urea are water-insoluble urea formaldehyde condensation products such as ureaform. Illustrative of useful water-insoluble urea and formaldehyde condensation products are those whose preparation and use are described in detail in U.S. Pat. Nos. 3,677,746 and 4,033,745.

The amount of urea or urea precursor compound included in the composition of this invention is not critical to the unique advantages thereof, and any amount known to those of skill in the art for use in fertilizers can be used. Normally, the amount employed will vary widely depending on a number of factors, including the times and frequency of application. In the preferred embodiments of the invention, the quantity of urea or urea precursor compound may vary from about 0.5 to about 95 weight percent based on the total weight of the composition and in the particularly preferred embodiments may vary from about 1 to about 50 weight percent on the same basis. In the most preferred embodiments of this invention, the quality of urea or urea precursor compound will vary from about 3 to about 40 weight percent on the aforementioned basis.

The fertilizer composition of this invention may include other optional ingredients known to those of skill in the art for inclusion in fertilizer compositions. For example, the composition may include sources of potassium, sulfur, phosphorus, boron, zinc, iron, manganese, copper, molybdenum, cobalt and like micronutrient and macronutrients which may be deficient in the soil. The composition may also include plant growth regulators, as for example auxins, cytokinins and the like, as well as pesticides, such as insecticides, miticides, herbicides, nematocides and the like.

The present invention can be carried out by distributing the one or more phosphorodiamide compounds in an unmodified form through growth medium. The present method also embraces distributing one or more such compounds as a constituent in liquid or finely divided solid compositions. In such practice the one or more phosphorodiamide compounds can be modified with one or more additaments or soil treating adjuvants including water, petroleum distillates or other liquid carriers, surface-active dispersing agents, inert finely divided solids and fertilizers such as urea or a compound capable of forming urea in situ. Preferred adjuvants are surface-active dispersing agents, inert finely divided solids, and especially, reduced nitrogen fertilizers; these adjuvants cooperate with the one or more phosphorodiamide compounds so as to facilitate the practice of the present invention and to obtain an improved result. Depending upon the concentration of the one or more phosphorodiamide compounds augmented compositions can be distributed in the soil without further modification or can be considered as concentrates and subsequently diluted with additional inert carrier to produce the ultimate treating composition. The required amount of the one or more phosphorodiamide compounds can be supplied to growth media in from 1 to 50 gallons of organic solvent carrier, in from 5 to 27,000 or more gallons of aqueous carrier or in from about 20 to 2000 pounds of solid carrier per acre treated. When an organic solvent carrier is employed, it can be further dispersed in the above volume of aqueous liquid carrier.

The concentration of one or more phosphorodiamide compounds in composition to be employed for the treatment of growth media is not critical and can vary considerably provided the required dosage of the effective agent is supplied to the growth media. In general, good results are obtained with liquid and solid compositions containing at least about 0.00001 percent by weight of the one or more phosphorodiamide compounds based on the total weight of the composition. In the preferred embodiments of the invention, the weight percent of one or more phosphorodiamide compounds contained in said composition is from about 0.00001 to about 98 percent or more on the aforementioned basis, and in the particularly preferred embodiments is from about 0.001 to about 50 weight percent also on the aforementioned basis. Amongst these particularly preferred embodiments, most preferred are those embodiments in which the weight percent of said compounds contained in said composition is from about 0.002 to about 20, and ideally from about 0.01 to about 10 weight percent. Liquid or solid compositions in which the one or more phosphorodiamide compounds are present in higher concentration can be utilized as such or can be employed as concentrate compositions to be diluted to prepare actual treating compositions.

Liquid compositions containing the desired amount of one or more phosphorodiamide compounds can be prepared by dispersing the latter in one or more liquid carriers, such as water or an organic solvent with or without the aid of a suitable surface active dispersing agent or emulsifying agent. Suitable organic solvents include acetone, diisobutylketone, methanol, ethanol, isopropyl alcohol, diethyl ether, toluene, methylene chloride, chlorobenzene and the petroleum distillates. The preferred organic solvents are those which are of such volatility that they leave little permanent residue in the growth media. Dispersing and emulsifying agents which can be employed in liquid compositions include condensation products of alkylene oxides with phenols and organic acids, alkyl aryl sulfonates, polyoxyalkylene derivatives of sorbitol esters, sugar esters, complex other alcohols, mahogany soaps and the like. The surface active agents are generally employed in the amount of from 1 to 20 percent by weight of one or more phosphorodiamide compounds.

Solid compositions containing the active one or more phosphorodiamide compounds can be prepared by dispersing the latter in finely divided inert solid carriers such as talc, chalk, gypsum, vermiculite, bentonite and the like, fuller's earth, attapulgite and other clays, various solid detergent dispersing agents and solid fertilizer compositions. In preparing such compositions, the carrier is mechanically ground with a solid one or more phosphorodiamide compounds wet with a liquid one or more phosphorodiamide compounds or a solution or dispersion of a solid or liquid one or more phosphorodiamide compounds in a volatile organic solvent. Depending upon the proportions of ingredients, these compositions can be employed without further modification or be considered concentrates and subsequently further diluted with solid surface active dispersing agent, talc, chalk, gypsum or the like to obtain the desired treating composition. Furthermore, such concentrate compositions can be dispersed in water with or without added dispersing agent or agents to prepare aqueous soil treating compositions.

Soil treating compositions can be prepared by dispersing one or more phosphorodiamide compounds in a urea fertilizer. The concentration employed in such compositions should, in general, be sufficient to substantially inhibit the hydrolysis of urea in the fertilizer to ammonia when the fertilizer is distributed in a plant growth medium. The resulting fertilizer composition can be employed as such or can be modified as by dilution with additional nitrogen fertilizer or with inert solid carrier to obtain a composition containing the desired amount of active agent for treatment of soil. Further, an aqueous dispersion of the one or more phosphorodiamide compounds fertilizer composition can be prepared and administered to the growth medium.

While the composition and method of this invention are particularly suited for agricultural applications for prevention or inhibition of urease catalyzed hydrolysis of urea, they can also be used in other applications where inhibition of the activity of urease is desired. For example, such other applications include use in animal litters, as feed additives, diaper treatment, pharmaceutical applications, urease inhibition in mammalian urinary tracts, and the like. It should be noted that the particular active compound employed in one application may not necessarily be useful in another application. Thus, in the selection of a particular active material for use in an application, such factors as toxicity of the material, the environment in which the material will be used, level of urease inhibition desired and the like must be considered in selecting such material.

The novel phosphorodiamide compounds of this invention which are useful as urease inhibitors in the composition and method of this invention are those of the formula:

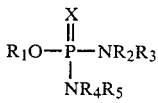

wherein

X is oxygen or sulfur;

$R_1$ is alkyl, aralkyl, alkenyl, heterocycle, cycloalkyl, cycloalkenyl, or alkynyl either unsubstituted or substituted with one or more halo, heterocycle, hydroxy, alkoxy, aryloxy, cyano, amino, dialkylamino, alkylamino, thiocyano, arylamino, acyloxy, quaternary ammonium radical, isocyanato, nitro, trihalomethyl, mercapto, alkanoyl, arylmercapto, isocyano, carboxyalkyl, alkylmercapto, $-ONO_2$, mercapto, $-SO_2OH$, $-OPO(OH)_2$, $-OB(OH)_2$ or $-OPO(OR)OH$, $-OPO(OR)_2$, $-OSO_2OR$, $-SO_2R$, and $-OSO_2R$ wherein R is aliphatic or aryl, or a combination thereof; and $R_2$, $R_3$, $R_4$ and $R_5$ are individually hydrogen, or alkyl having from 1 to 4 carbon atoms.

Illustrative of permissible $R_1$ substituents are unsubstituted or substituted straight and branched chain alkyl such as 2-chloroethyl, 3-chloropropyl, 4-chlorobutyl, methyl, 3-iodopropyl, 2-cyanoethyl, iodomethyl, 2-phenoxyethyl, 3-bromopentyl, 5-chloropentyl, 2-methoxyneopentyl, 2-iodo-2-phenylethyl, 4-isopropoxyethyl, benzyl, 2-naphthoxyethyl, 2,2-dichloropropyl, 3-mercaptobutyl, 2-acetylpropyl, ethyl, 2-cyanoethyl, 3-phenoxypropyl, 2-hydroxyethyl, 2-phenylmercaptoethyl, and the like; substituted or unsubstituted straight and branched chain alkenyl, such as allyl, 2-propenyl, 2-chloroprop-2-enyl, 1-chloro-prop-2-enyl, 2-cyanobut-3-enyl, trichlorovinyl, dichlorovinyl, dichloroallyl, trichloroallyl, 3-methoxypent-4-enyl, 1-iodo-2,2-dimethylprop-2-enyl, and the like; and substituted straight and branched chain alkynyl such as acetylene, 2-chloroprop-2-yl, 3-bromoprop-2-yl, propynyl, and the like; substituted and unsubstituted cycloalkyl and cycloalkenyl such as cyclobutyl, cyclohexyl, cyclopentyl, cyclohexenyl, 2-chlorocyclohexyl, 3-cyanocyclopentyl, 2,2-difluorocyclohexenyl, 2-hydroxycyclohexyl and the like; and aralkyl such as benzyl, 2-phenylethyl, 2-phenylpropyl, 2-naphthylethyl, 3-phenylbutyl, 4-phenylhexyl and the like.

Examples of useful $R_2$, $R_3$, $R_4$ and $R_5$ substituents are hydrogen and alkyl such as methyl, ethyl, propyl and butyl.

The following compounds are illustrative of phosphorodiamide compounds within the scope of the generic formula set forth above which can be prepared in accordance with the procedures set forth hereinbelow and which can be employed in the practice of this invention.

2-phenylthioethyl phosphorodiamidate
2-phenoxyethyl phosphorodiamidate
2-cyanoethyl phosphorodiamidate
2-(dimethylamino)ethyl phosphorodiamidate
2-(phenacyl)ethyl phosphorodiamidate
1-chloro-2-propenyl phosphorodiamidate
2-(phenylsulfonyl)ethyl diamidophosphorothionate
2-nitroethyl N-methyl phosphorodiamidate
hydroxymethyl phosphorodiamidate
2-chloroethyl phosphorodiamidate
methoxymethyl phosphorodiamidate
benzyl phosphorodiamidate
hexyl phosphorodiamidate
2-propenyl phosphorodiamidate
4-hexenyl phosphorodiamidate
cyclohexenyl phosphorodiamidate
cyclopentenyl phosphorodiamidate
3-naphthylpropyl phosphorodiamidate
2-(2,3-dimethylphenyl)ethyl phosphorodiamidate
(2,4-dichlorophenyl)methyl phosphorodiamidate
(4-trifluoromethylphenyl) methyl phosphorodiamidate
2-hexanoylethyl phosphorodiamidate
3-chloro-2-propenyl phosphorodiamidate
3-chloro-2-propenyl phosphorodiamidate
2-(4-methoxyphenyl)ethyl phosphorodiamidate
dichloromethyl diamidophosphorothionate
trichloromethyl diamidophosphorothionate
2,2-difluoroethyl diamidophosphorothionate
3-hydroxy-2-chloropropyl diamidophosphorothionate
2-(4-mercaptophenyl) ethyl diamidophosphorothionate
2-(4-phenylthiophenyl) propyl phosphorodiamidate
(4-phenoxyphenyl) methyl phosphorodiamidate
3-cyanopropyl diamidophosphorothionate
2-phenoxyethyl diamidophosphorothionate
2-acetylpropyl phosphorodiamidate
2-phenylmercaptoethyl diamidophosphorothionate
2-chloropropyl phosphorodiamidate
2,2-diiodopropyl diamidophosphorothionate
2,2-difluoroethyl phosphorodiamidate
cyclopentyl phosphorodiamidate
cyclopropyl phosphorodiamidate
2-propynyl phosphorodiamidate
3-chloro-2-propynyl diamidophosphorothionate
3-phenylpropyl phosphorodiamidate
3-thienyl phosphorodiamidate
3-pyridyl phosphorodiamidate
2-pyrrolidyl diamidophosphorothionate
2-furyl phosphorodiamidate
3-furyl phosphorodiamidate
3-pyranyl phosphorodiamidate
furfuryl phosphorodiamidate
2-furoyl phosphorodiamidate
imidazolyl diamidophosphorothionate
imidazolidyl phosphorodiamidate
indanylmethyl phosphorodiamidate
2-(indenyl) ethyl phosphorodiamidate
3-(indolyl) propyl phosphorodiamidate
isobutoxymethyl phosphorodiamidate
isoamoxyethyl diamidophosphorothionate
2-(isobutyryl)propyl diamidophosphorothionate
isocyanomethyl phosphorodiamidate
3-isocyanatopropyl phosphorodiamidate
2-oxazolyl phosphorodiamidate
4-pyrazinyl phosphorodiamidate
5-thiadiazolidyl phosphorodiamidate
3-pyrazolidyl diamidophosphorothionate 3-pyrazolyl phosphorodiamidate
pyrroyl phosphorodiamidate
2-pyrimidyl phosphorodiamidate
2-thiocyanomethyl phosphorodiamidate
3-thiazolidyl phosphorodiamidate
4-thiazolidyl phosphorodiamidate
2-(2-toluyl)ethyl phosphorodiamidate
3-formamidopropyl phosphorodiamidate
cyclobutyl phosphorodiamidate
2-(2,4-dihydroxyphenyl)ethyl phosphorodiamidate
octyl phosphorodiamidate
methylphosphorodiamidate
ethylmercaptomethyl phosphorodiamidate
2-(butanoyl)ethyl phosphorodiamidate
2-(benzothiazole) phosphorodiamidate
2-(benzofuranyl) phosphorodiamidate
3-(benzothienyl) diamidophosphorothionate
thiocarbamoylethyl diamidophosphorothionate
2-methyl-4-pyrone-3-phosphorodiamidate
6-methyl-2-pyrone-4-phosphorodiamidate
crotonyl phosphorodiamidate
2-pyrimidyl phosphorodiamidate
5,6,7,8-tetrahydronaphthylenyl phosphorodiamidate
propargyl phosphorodiamidate
2-benzimidazole phosphorodiamidate
dodecylphosphorodiamidate
nonyl phosphorodiamidate
oleyl phosphorodiamidate
3-quinolinyl phosphorodiamidate
pyrazinyl phosphorodiamidate Preferred for use in the practice of this invention are phosphorodiamide compounds in which:

X is oxygen;

$R_1$ is alkyl, alkenyl, or aralkyl, either unsubstituted or substituted with one or more substituents at the alpha, beta and/or gamma carbon atoms relative to the oxygen atom to which the $R_1$ group is substituted; and $R_2$, $R_3$, $R_4$ and $R_5$ are individually hydrogen or methyl.

Particularly preferred for use in this invention are compounds in which:

X is oxygen;

$R_1$ is alkyl having from 1 to about 7 carbon atoms, alkenyl having from 2 to about 7 carbon atoms, or phenylalkyl having from 7 to about 14 carbon atoms either unsubstituted or substituted with one or more substituents on the alpha, beta and/or gamma carbon atoms relative to the oxygen atom wherein permissible substituents are selected from the group consisting of iodo, chloro, bromo, fluoro, phenoxy, p-nitrophenoxy, or —$OSO_2OR$ and —$OSO_2R$ wherein R is alkyl or phenyl; and $R_2$, $R_3$, $R_4$ and $R_5$ are hydrogen.

Among these particularly preferred compounds, most preferred are those compounds in which:

X is oxygen;

$R_1$ is alkyl having up to about 3 carbon atoms substituted with one or more halo, phenoxy, p-nitrophenoxy or nitro groups on the alpha, beta and/or gamma carbon atom relative to the oxygen atom; and $R_2$, $R_3$, $R_4$ and $R_5$ are hydrogen.

Especially effacious compounds for use in the practice of this invention are 3-chloropropyl phosphorodiamidate; 2,2,2-trifluoroethyl phosphorodiamidate; 2,2,2-trichloroethyl phosphorodiamidate; 2-bromoethyl phosphorodiamidate; 2-chloroethyl phosphorodiamidate; cyclohexyl phosphorodiamidate; allyl phosphorodiamidate; benzyl phosphorodiamidate; 1,3-dichloro-2-propyl phosphorodiamidate; and 2,2,6,6-tetrachlorocyclohexyl phosphorodiamidate.

Useful compounds can be prepared in accordance with the following reaction scheme:

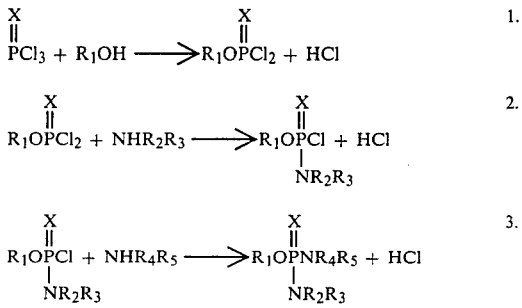

in which X, $R_1$, $R_2$, $R_3$, $R_4$, $R_5$ are as defined hereinabove.

The aforementioned reaction is described in more detail in East German Pat. No. 128,315, Roth, H. J., et al., SYNTHESIS OF PHENYL PHOSPHORODIAMIDATES. PART I., Arch. Pharm., vol. 314, pp. 85–91, 1980, and references cited therein, and E. Cherbuliez in "Organic Phosphorus Compounds", ed. G. M. Kosolopoff and L. Maier, Vol. 6 Chap. 15, Wiley-Interscience, 1973, and E. Fluck and W. Haubold, ibid., Chapter 16. Accordingly this will not be described herein in any great detail.

Briefly stated, in each step of the three step reaction sequence, substantially equal molar amounts of the reactants are contacted, or excesses of the reactants can be used. The contacting is preferably neat or in an inert solvent, and optionally and in the presence of a hydrogen chloride acceptor. Inert solvents which can be used in this reaction include benzene, ethyl ether, toluene, tetrahydrofuran, xylene, dioxane, methylene chloride, dimethylformamide, carbon tetrachloride, methyl sulfoxide and the like.

Useful hydrogen chloride acid acceptors can be either inorganic or organic bases. Suitable acid acceptors include alkali metal carbonates such as sodium and potassium carbonates, but preferably tertiary amines such as pyridine, triethylamine, trimethylamine, isoquinoline, lutidine, tributylamine, 1,4-diazabicyclo[2,2,2]octane, N-ethyl piperidine, quinoline and the like. Alternatively, an excess of the amine reactant is used as the acid acceptor.

Reaction temperatures are not critical and can be varied widely. For example, the reaction can be conveniently carried out in a temperature of from about $-20°$ C. to about 200° C., but is preferably carried out at a temperature of from about 25° C. to about 125° C.

Similarly, reaction pressures are not critical and can be varied widely. For example, the reaction can be carried out at sub-atmospheric, atmospheric or superatmospheric pressure. However, for convenience, the reaction is carried out at atmospheric or autogeneous pressure.

The order in which the various amines and the alcohol are reacted as indicated in the above reaction sequence is only for illustrative purposes, and order of reaction is not critical.

The exact proportions of the reactants are not critical, some of the desired product being obtained when the reactants are employed in any proportions. However, in going to completion, the reaction consumes the reactants and the hydrogen chloride acceptor in equimolar proportions and the use of the reactants and the hydrogen chloride acceptor in such proportions is preferred.

Reaction times are not critical and can vary widely, depending on a number of factors including but not limited to reaction temperature, and the reactivities of the various reactants. The mixture is held within the desired reaction temperature range for a period of time, conveniently from about 2 to 8 hours before cooling. Good yields are obtained with reaction times of about 4 to 5 hours.

During the reaction, the hydrochloride salt of the hydrogen chloride acceptor forms and may precipitate from the mixture. This salt can be removed by such conventional procedures as extraction, filtration or centrifugation. The phosphorodiamide compound can be separated by such conventional procedures as evaporation and purified by conventional procedures such as distillation and extraction. The product separated as described above may be employed in the control of urease in soil or may be further purified by conventional procedures such as extraction and distillation.

The following specific examples are presented to more particularly illustrate the invention.

EXAMPLE I

The Preparation of 3-Chlororopyl Phosphorodichloridate

A 250 mL flask was charged with 100 mL of $CH_2Cl_2$ and 18 mL of $POCl_3$ (0.2 mol). To this mixture was added at room temperature over 30 min, a solution of 10.0 g of (0.10 mol) 3-chloro-1-hydroxypropane in 25 mL of $CH_2Cl_2$. The solution was then refluxed overnight under nitrogen. Distillation gave 19.4 g (87%) of a clear, colorless liquid, bp 64° C. at 0.1–0.15 mm.

NMR ($CDCl_3$): $\delta 4.5$ (dt, 2H, $J_{CH_2CH_2O}=6$ Hz; $J_{CH_2OP}=10$ Hz); 3.7 (t, 2H), 2.25 (doublet of quintets, 2H, $J_{CH_2CH_2OP}=1.5$ Hz); and IR (neat): 2985, 1300, 1020 cm$^{-1}$.

EXAMPLE II

The Preparation of 3-Chloropropyl Phosphorodiamidate

A solution of 19.1 g of (0.09 mol) 3-chloropropyl phosphorodichloridate in 25 mL of $CH_2Cl_2$ was added to a solution of 10 g of (0.59 mol) $NH_3$ in 150 mL of $CH_2Cl_2$ at $-15°$ to $-30°$ C. After the addition, the mixture was allowed to warm slowly to room temperature, while the excess $NH_3$ vented. Filtering gave 24.9 g of crude material consisting of the desired product and $NH_4Cl$ (theoretical yield 25.2 g). Pure 3-chloropropyl phosphorodiamidate was obtained by extraction with methylene chloride. The 3-chloropropyl phosphorodiamidate product after drying over $P_2O_5$ had mp 111°–112° C.

Anal. Calcd. for $C_3H_{10}ClN_2O_2P$: C, 20.88; H, 5.84; N, 16.23%, Found: C, 20.88; H, 6.00; N, 16.15%; and NMR (DMSO-$d_6$/$D_2O$): $\delta 3.6-4.1$ (m, 8H, includes singlet for $NH_2$), 2.0 (quintet, 2H).

EXAMPLE III

The Preparation of Allyl Phosphorodiamidate

To a solution of 18.1 g of (0.118 mol) $POCl_3$ in 100 mL of dry ether held at a temperature of 5° C. was added a solution of 10.6 g (0.105 mol) of triethylamine in 15 mL of ether, followed by addition of a solution of 5.9 g (0.102 mol) allyl alcohol in 10 mL ether at 3°–9° C. over a period of 30 min. The resultant solution was stirred 15 min. and filtered. The volatiles were removed under reduced pressure to give 15.4 g of a pale yellow oil. Distillation was not attempted, but the crude oil was treated with $NH_3$ (10 g) in 150 mL of $CH_2Cl_2$ at $-30°$ to $-40°$ C. After warming to room temperature, the mixture was filtered and 18.7 g of a white solid was collected. The resultant solid was extracted with $CH_2Cl_2$ (Soxhlet) to give 6.2 g of (45% from allyl alcohol) glistening white crystals, mp 120°–124° C.

NMR (DMSO-$D_6$/$D_2O$): $\delta 5.65-6.15$ (m, 1H), 5.05–5.4 (m, 2H), 4.2–4.4 (m, 2H), 4.0 (s, 4H);

IR (nujol): 3340, 3230, 3120, 1645, 1570, 1170 cm$^{-1}$; and

Anal. Calcd. for $C_3H_9N_2O_2P$: C, 26.45; H, 6.67; N, 20.59% Found: C, 26.19; H, 6.68; N, 20.47%.

EXAMPLE IV

The Preparation of 2,2,2-Trifluoroethyl Phosphorodiamidate

To a solution of 17.3 g (0.113 mol) of $POCl_3$ in 50 mL of toluene held at 0° C. was added 7.9 g (0.10 mol) of pyridine, followed by addition of 10.0 g (0.10 mol) of trifluoroethanol, at a rate to maintain the temperature of the mixture at 0°–10° C. The mixture was stirred one hour at ice bath temperature, and then overnight at room temperature. After filtering, the solution was distilled to give the desired 2,2,2-trifluoroethyl phosphorodichloridate, bp 140°–146° C. The dichloridate, 4.5 g (0.21 mol) was treated with 10 g $NH_3$ in 50 mL $CH_2Cl_2$ at $-40°$ C. After warming to room temperature, the product was filtered and purified by Soxhlet extraction with $CH_2Cl_2$ for two days. After drying over $P_2O_5$, the 2,2,2-trifluoroethyl phosphorodiamidate had mp 142°–144° C.

NMR (DMSO-$d_6$): $\delta 4.0-4.5$ (m); and

IR (nujol): 1310, 1280, 1175, 963 cm$^{-1}$.

EXAMPLE V

The Preparation of 2,2,2-Trichloroethyl Phosphorodiamidate

To 90 g (0.59 mol) of $POCl_3$ at 25° C. was slowly added 72 g (0.48 mol) of 2,2,2-trichloroethanol over a two hour period. The mixture was heated and maintained at 100°–125° C. for 14 hours during which time 22 g (0.60 mol) of HCl was recovered in the water scrubber. The mixture was distilled to give 72 g (0.27 mol) of 2,2,2-trichloroethyl phosphorodichloridate, bp 84° C. at 3 mm (57% yield).

The dichloridate (31 g, 0.12 mol) in 25 mL $CHCl_3$ was slowly added to 20 g (1.40 mol) of $NH_3$ dissolved in 50 mL $CHCl_3$ at $-25°$ C. After warming to room temperature, the mixture was filtered to remove $NH_4Cl$ by-product, and the desired product recrystallized from $CHCl_3$ to give 21 g (0.094 mol) of desired 2,2,2-trichloroethyl phosphorodiamidate, mp 86°–87° C. (78% yield)).

NMR (DMSO-$d_6$/$D_2O$): $\delta 4.4$ (d, 2H, J=5 Hz), 4.25 (S, 4H); and

IR (nujol): 1185 cm$^{-1}$.

EXAMPLE VI

The Preparation of 2-Bromoethyl Phosphorodiamidate

2-Bromoethanol (18.9 g) was added to 47.2 g of $POCl_3$ and the mixture heated to 60°–65° C. until HCl evolution ceased (1.5 h). The reaction mixture was then distilled, to provide the desired 2-bromoethyl phosphorodichloridate having a bp of 90°–92° C. at 0.25 mm. The 2-bromoethyl phosphorodichloridate (15 g, 0.062 mol) was added to 12 g of $NH_3$ in 50 mL of $CH_2Cl_2$ at −20° C. After warming to room temperature, the solids were filtered. Pure product was obtained by Soxhlet extraction of the crude solid using $CH_2Cl_2$ (60% yield), mp 110°–111° C.

NMR ($D_2O$): $\delta 3.6$ (t, 2H), 4.2 (m, 2H), 4.7 (s, 4H).

EXAMPLE VII

The Preparation of 2-Chloroethyl Phoshorodiamidate

2-Chloroethanol (12.1 g, 0.15 mol) was added to 46.6 g (0.304 mol) of $POCl_3$, and the mixture heated to 60°–70° C. until HCl evolution ceased (1.5 h). The mixture was then distilled to give 20.3 g of a colorless liquid bp 106°–108° C. at 1.7 mm. A solution of 15 g of the compound obtained above in 50 mL of $CH_2Cl_2$ was added to a solution of 12 g of $NH_3$ in 200 mL of $CH_2Cl_2$ at −20° C. After warming to room temperature, the crude product was filtered (19.9 g). The solid product was taken up in 300 mL of fresh $CH_2Cl_2$ containing 16 mL of diethylamine, and the mixture refluxed overnight. The treatment was repeated, before collecting the pure product by filtration (8.0 g), mp 122°–123° C.

NMR (DMSO-$d_6$): $\delta 3.2-4.1$ (m). In $D_2O$, there is a triplet (2H), doublet of triplets (2H), and a singlet (4H).

EXAMPLE VIII

The Preparation of 1,3-Dichloro-2-propyl Phosphorodiamidate

To 85 g (0.56 mol) of $POCl_3$ at 25° C. was slowly added 64.5 g (0.50 mol) of 1,3-dichloro-2-propanol over a 2 hour period. The mixture was heated to 120° C. for 12 hours during which time 21 g (0.57 mol) of HCl was recovered in the water scrubber. The mixture was distilled and 50 g (0.20 mol) of 1,3-dichloro-2-propylphosphorodichloridate, bp 105°–110° C. at 5 mm was recovered in 40.6% yield.

The dichloridate, 25 g (0.10 mol), in 25 mL $CHCl_3$ was slowly added to 17 g (1.0 mol) of $NH_3$ in 50 mL $CHCl_3$ at −25° C. After warming to room temperature, the mixture was filtered to remove $NH_4Cl$. The product was recrystallized from $CHCl_3$ to give 15 g (0.072 mol) of desired 1,3-dichloro-2-propylphosphorodiamidate, mp 70°–72° C. (71% yield).

EXAMPLE IX

The Preparation of Benzyl Phosphorodiamidate

To a 0° C. solution of 25.1 g (0.16 mol) of $POCl_3$ in 100 mL of dry ether was added a solution of 10.6 g (0.105 mol) of triethylamine in 15 mL of ether over a period of 10 min followed by the cautious addition of 10.8 g (0.10 mol) benzyl alcohol in 15 mL of ether over a period of 0.5 hr at 0.10° C. The solution was stirred for 60 min. and filtered. The volatiles were removed under reduced pressures to provide 26.5 g of a crude oil. The product was treated with $NH_3$ (12 g) in 150 mL of $CH_2Cl_2$ at −30° C. After warming to room temperature, the mixture was filtered to provide 28 gm of a solid material. The impure product was washed with water followed by a methanol washing. After drying the product had a mp of 166°–167° C.

NMR (DMSO-$d_6$/$D_2O$): $\delta 7.33$ (s, 5H), 4.8 (d, 2H, J=6–7 Hz), 3.8 (s, 4H).

EXAMPLE X

The Preparation of Methyl Phosphorodiamidate

To a solution of 43 g (2.25 mol) of ammonia dissolved in 50 mL $CHCl_3$ at −25° C. was slowly added 37 g (0.25 mol) of methyl phosphorodichloridate in 25 mL $CHCl_3$. After warming to room temperature, the mixture was filtered to provide 25 g of a solid material which was a mixture of $NH_4Cl$ and the desired methyl phosphorodiamidate. The mixture was tested for urease inhibition without further purification.

EXAMPLE XI

The Preparation of Propyl Phosphorotriamidate

To a 0° C. solution of 47 g (0.31 mol) $POCl_3$ in 150 mL $CH_2Cl_2$ was added, over a period of 35 minutes, a solution of 9.0 g (0.15 mol) n-propanol in 50 mL $CH_2Cl_2$. The solution was warmed to 30°–45° C. for 2.5 h, during which time HCl evolved. Distillation afforded 22.9 g (86%) of propyl phosphorodichloridate bp 84°–85° C. at 2.2 mm. The dichloridate (17.7 g) was treated with 12 g $NH_3$ in 200 mL $CH_2Cl_2$ at −20° C. After warming to room temperature, the mixture was filtered to provide 24 g of a white solid. The impure product was refluxed in $CH_2Cl_2$ with 1.5 equivalents of diethylamine until $NH_3$ evolution ceased. The pure product was then collected by filtration in 39% yield, mp 140°–142° C.

NMR (DMSO-$d_6$): $\delta 3.5-4.0$ (m, $CH_2O$ and $NH_2$, 6H), 1.55 (m, 2H), 0.9 (t, 3H).

EXAMPLE XII

Preparation of Cyclohexylphosphorodiamidate

Cyclohexanol (6.1 ml, 6.01 g, 60 m mol) was added to heated (50°–60° C.) phosphorous oxychloride (9.3 ml, 15.3 g, 100 m mol) under nitrogen, and evolution of HCl gas was observed. After the addition, the reaction mixture was heated to 80°–90° C. for 45 minutes, cooled, and distilled. The fraction boiling at 65°–74° C. at 5 torr (1.9 g, 15% yield) is the desired cyclohexyl phosphorodichloridate.

IR (neat): 2935 and 2860 ($CH_2$), 1325 (P=O) $cm^{-1}$.

Cyclohexyl phosphorodichloridate (1.8 g, 8.3 m mol) was dissolved in anhydrous ether (50 ml) and the solution added to a saturated solution of ammonia in ether (250 ml) at 0° C. A white precipitate formed which was a mixture of the desired cyclohexyl phosphorodiamidate (62.5%) and ammonium chloride (37.5%) was separated by filtration, washed with ether, and dried in vacuum, weight 1.9 g.

EXAMPLE XIII

Preparation of 2,2,6,6-Tetrachlorocyclohexyl Phosphorodiamidate

The alcohol 2,2,6,6-tetrachlorocyclohexanol (11.9 g, 50 m mol) and phosphorus oxychloride (6.0 ml, 9.9 g, 65 m mol) were dissolved in 200 ml of anhydrous ether under nitrogen. The solution was cooled to −10° C., and pyridine (4.0 ml, 50 m mol) in 20 ml of ether was added. The reaction mixture was allowed to warm to room temperature with stirring. The precipitated solid was collected by filtration. The filtrate was added to a saturated solution of ammonia in ether at 0° C. (500 ml), to provide a white solid which was dried in vacuum, weight 13.6 g. The pure product was obtained by extraction with methylene chloride.

'H NMR (pyridine-d$_5$): δ4.6–6.3 (br, 4H, NH), 4.6 (S, 1H, CH), 1.3–3.0 (m, 6H, CH$_2$);
IR (KBr): 3445 and 3290 (NH), 1210 and 1110 (P=O) cm$^{-1}$.

EXAMPLE XIV

Several phosphorodiamidate compounds were evaluated to determine their efficacy as urease inhibitors. The inhibition tests were run in a New York soil (Cazenovia sandy loam, pH 7.2) or in Wisconsin soil (Plano silt loam, pH 5.4). Evaluations (run in triplicate) consisted of applying 800 micrograms of test compound in 5 mL of water and 42.8 mg of urea in 1 mL of water to a 20 g of air-dry soil in a glass bottle. The bottle was capped with perforated aluminum foil and incubated at 25° C. for three days prior to extraction with 100 mL of a 2M KCl solution containing 0.5 mg phenylmercuric acetate. The extracts were then analyzed for remaining urea using an autoanalyzer. Percent inhibition was calculated as $$\% \text{ Inhibition} = [1 - (A - B/B - C)] \times 100$$

where A is urea recovered from unincubated sample (urea added to soil and immediately extracted); B is urea recovered from inhibited sample; and C is urea recovered from the control (uninhibited sample).

The results of these tests are set forth in the following Table I.

TABLE I

Urease Inhibition By Phosphorodiamidate Compounds, ROPO(NH$_2$)$_2$

| Experiment | R | % Inhibition Cazenovia Soil | % Inhibition Wisconsin Soil |
|---|---|---|---|
| 1 | 2,2,2-Trifluoroethyl | 97 | 90 |
| 2 | 2,2,2-Trichloroethyl | 97 | 87 |
| 3 | 2-Bromoethyl | 85 | — |
| 4 | 2-Chloroethyl | 84 | — |
| 5 | 1,3-Dichloro-2-propyl | 72 | 49 |
| 6 | Allyl | 65 | 38 |
| 7 | Benzyl | 69 | 20 |
| 8 | 3-Chloropropyl | 41 | 22 |
| 9 | Methyl | 34 | — |
| 10 | Propyl | 15 | — |
| 11 | Cyclohexyl | 85 | — |
| 12 | 2,2,6,6-Tetrachlorocyclohexyl | 38 | — |

What is claimed is:

1. A composition comprising an acceptable carrier and a urease inhibiting effective amount of one or more phosphorodiamide compounds of the formula:

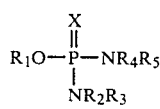

wherein
X is oxygen or sulfur;
R$_1$ is alkyl, aralkyl, alkenyl, heterocycle, cycloalkyl, cycloalkenyl or alkynyl, either unsubstituted or substituted with one or more halo, heterocycle, hydroxy, alkoxy, alkylmercapto, carboxyalkyl, quaternary ammonium radical, arylmercapto, aryloxy, cyano, acyloxy, —ONO$_2$, nitro, alkylamino, amino, arylamino, dialkylamino, alkanoyl, isocyanato, isocyano, mercapto, —SO$_2$OH, —OPO(OH)$_2$, —OB(OH)$_2$ or —OPO(OR)OH, —OPO(OR)$_2$, —OSO$_2$OR, —SO$_2$R and —OSO$_2$R wherein R is aliphatic or aryl, or a combination thereof; and
R$_2$, R$_3$, R$_4$ and R$_5$ are the same or different and are individually hydrogen or alkyl having from 1 to 4 carbon atoms.

2. A composition according to claim 1 wherein said urease inhibiting effective amount is at least about 0.00001 weight percent based on the total weight of the composition.

3. A composition according to claim 2 wherein said amount is from about 0.00001 to about 98 weight percent.

4. A composition according to claim 3 wherein said amount is from about 0.001 to about 50 weight percent.

5. A composition according to claim 4 wherein said amount is from about 0.002 to about 20 weight percent.

6. A composition according to claim 5 wherein said amount is from about 0.01 to about 10 weight percent.

7. A composition according to claim 1 wherein X is oxygen.

8. A composition according to claim 1 wherein R$_2$, R$_3$, R$_4$ and R$_5$ are the same or different and are individually hydrogen or methyl.

9. A composition according to claim 8 wherein R$_2$, R$_3$, R$_4$ and R$_5$ are hydrogen.

10. A composition according to claim 1 wherein R$_1$ is substituted or unsubstituted alkyl, cyclohexyl, alkenyl or aralkyl.

11. A composition according to claim 10 wherein R$_1$ is substituted alkyl having from 1 to about 7 carbon atoms.

12. A composition according to claim 11 wherein R$_1$ is substituted or unsubstituted methyl, ethyl, propyl, or butyl.

13. A composition according to claim 10 wherein R$_1$ is substituted or unsubstituted alkenyl having from 1 to 7 carbon atoms.

14. A composition according to claim 13 wherein R$_1$ is allyl.

15. A composition according to claim 10 wherein R$_1$ is substituted or unsubstituted cycloalkyl.

16. A composition according to claim 15 where R$_1$ is substituted or unsubstituted cyclopropyl, cyclopentyl or cyclohexyl.

17. A composition according to claim 16 wherein R$_1$ is cyclohexyl or cyclohexyl substitued with one or more halo substituents.

18. A composition according to claim 17 wherein R$_1$ is cyclohexyl.

19. A composition according to claim 10 wherein R$_1$ is aralkyl.

20. A composition according to claim 19 wherein R$_1$ phenylalkyl having from 7 to about 14 carbon atoms.

21. A composition according to claim 20 wherein R$_1$ is benzyl.

22. A composition according to claim 11 wherein R$_1$ is alkyl substituted with one or more substituents at the alpha, beta and/or gamma carbon atoms relative to the oxygen atom to which R$_1$ is substituted.

23. A composition according to claim 22 wherein R$_1$ is alkyl having from 1 to 3 carbon atoms substituted at the alpha and/or beta carbon atoms.

24. A composition according to claim 23 wherein said permissible substituents are selected from the group consisting of alkoxy, hydroxy, cyano, nitro, halo, and phenoxy.

25. A composition according to claim 24 wherein said permissible substituents are cyano, halo and phenoxy.

26. A composition according to claim 25 wherein said permissible substituent is halo.

27. A composition according to claim 26 wherein $R_1$ is alkyl having more than one halo substituent substituted at the alpha, beta and/or gamma position.

28. A composition according to claim 26 wherein said alkyl is methyl or ethyl.

29. A composition according to claim 28 wherein said permissible substituent is chloro, bromo or iodo.

30. A composition according to claim 29 wherein $R_1$ is ethyl having one or more substituents on the beta and/or alpha carbon atoms.

31. A composition according to claim 26 wherein said $R_1$ selected from the group consisting of 2-haloethyl, 2,2-dihaloethyl, 2,2,2-trihaloethyl, halomethyl, dihalomethyl, trihalomethyl, 2-halopropyl, 2,2-dihalopropyl, 2-halobutyl and 2,2-dihalobutyl.

32. A composition according to claim 1 wherein:
X is oxygen;
$R_1$ is alkyl, cycloalkyl, alkenyl or aralkyl either unsubstituted or substitued with one or more halo, cyano, nitro or hydroxy substituents; and
$R_2$, $R_3$, $R_4$ and $R_5$ are hydrogen.

33. A composition according to claim 32 wherein:
X is oxygen;
$R_1$ is alkyl having from 1 to about 4 carbon atoms, alkenyl having from 2 to about 4 carbon atoms, phenylalkyl having from 7 to about 12 carbon atoms, cyclopropyl, cyclobutyl, cyclopentyl or cyclohexyl, either unsubstituted or substituted with one or more halo groups; and
$R_2$, $R_3$, $R_4$ and $R_5$ are hydrogen.

34. A composition according to claim 1 wherein said one or more phosphorodiamide compounds are selected from the group consisting of 3-chloropropyl phosphorodiamidate; 2,2,2-trifluoromethyl phosphorodiamidate; 2,2,2-trichloromethyl phosphorodiamidate; 3-bromoethyl phosphorodiamidate; 2-chloroethyl phosphorodiamidate; and cyclohexyl phosphorodiamidate.

35. A composition according to claim 34 wherein said compounds are selected from the group consisting of 2,2,2-trifluoromethyl phosphorodiamidate; 2,2,2-trichloromethyl phosphorodiamidate and cyclohexyl phosphorodiamidate.

36. An improved fertilizer composition comprising urea, or one or more urea precursor compounds which are capable of forming urea in situ when subjected to the use conditions of the composition, and a urease inhibiting effective amount of one or more phosphorodiamide compounds of the formula:

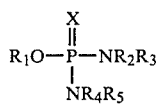

wherein
X is oxygen or sulfur;
$R_1$ is alkyl, aralkyl, alkenyl, heterocycle, cycloalkyl, cycloalkenyl, or alkynyl either unsubstituted or substituted with one or more halo, heterocycle, alkylmercapto, hydroxy, alkoxy, aryloxy, cyano, acyloxy, $-ONO_2$, mercapto, $-SO_2OH$, alkanoyl, nitro, amino, carboxyalkyl, alkylamino, dialkylamino, arylamino, isocyanato, isocyano, quaternary ammonium radical, arylmercapto, $-OPO(OH)_2$, $-OB(OH)_2$ or $-OPO(OR)OH$, $-OPO(OR)_2$, $-OSO_2OR$, $-SO_2R$ and $-OSO_2R$ wherein R is aliphatic or aryl, or a combination thereof; and
$R_2$, $R_3$, $R_4$ and $R_5$ are individually hydrogen, or alkyl having from 1 to about 4 carbon atoms.

37. A method of enhancing plant growth and crop yield which comprises applying an effective amount of the composition according to claim 36 to the plant growth media within the root zone of said plant.

38. A method of inhibiting the urease catalyzed hydrolysis of urea at a situs which comprises applying to said situs a urease inhibiting effective amount of one or more phosphorodiamide compounds of the formula:

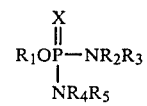

wherein:
X is oxygen or sulfur;
$R_1$ is alkyl, aralkyl, alkenyl, heterocycle, cycloalkyl, cycloalkenyl, or alkynyl either unsubstituted or substituted with one or more alkanoyl, heterocycle, nitro, amino, alkylamino, dialkylamino, arylamino, carboxyalkyl, isocyanato, isocyano, halo, hydroxy, alkoxy, aryloxy, cyano, acyloxy, $-ONO_2$, mercapto, alkylmercapto, $-SO_2OH$, quaternary ammonium radical, arylmercapto, $-OPO(OH)_2$, $-OB(OH)_2$ or $-OPO(OR)OH$, $-OPO(OR)_2$, $-OSO_2OR$, $-SO_2R$ and $-OSO_2R$ wherein R is aliphatic or aryl, or a combination thereof; and
$R_2$, $R_3$, $R_4$ and $R_5$ are individually hydrogen, or alkyl having from 1 to about 4 carbon atoms.

39. A method according to claim 38 wherein said one or more phosphorodiamide compounds are applied to said situs prior to, subsequent to or in conjunction with the application to said situs of urea or one or more urea precursor compounds capable of forming urea in situ in said media.

40. A method according to claim 39 wherein said situs is a plant growth medium.

41. A method according to claim 38 wherein said urease inhibiting effective amount is at least about 0.01 ppm.

42. A method according to claim 41 wherein said amount is from about 0.01 to about 5000 ppm.

43. A method according to claim 42 wherein said amount is from about 2 to about 1000 ppm.

44. A method according to claim 43 wherein said amount is from about 10 to about 500 ppm.

45. A composition according to claim 1 wherein said carrier is a liquid.

46. A composition according to claim 45 wherein said liquid carrier is selected from the group consisting of water and organic liquids.

47. A composition according to claim 1 wherein said carrier is a finely divided inert solid.

48. A composition according to claim 1 wherein X is sulfur.

* * * * *